United States Patent [19]

Apter

[11] Patent Number: 5,072,107
[45] Date of Patent: Dec. 10, 1991

[54] APPARATUS FOR EXAMINING THE MOUTHS OF BOTTLES OR THE LIKE

[75] Inventor: Robert Apter, Rudolfstetten, Switzerland

[73] Assignee: Elpatronics AG, Zug, Switzerland

[21] Appl. No.: 580,220

[22] Filed: Sep. 10, 1990

[30] Foreign Application Priority Data

Oct. 6, 1989 [CH] Switzerland ............... 3664/89

[51] Int. Cl.5 .................. G01N 9/04; G06M 7/00; H01J 40/14
[52] U.S. Cl. .................. 250/223 B; 356/240; 209/526
[58] Field of Search .......... 250/223 B, 227.11; 356/239, 240, 428; 358/106; 209/526

[56] References Cited

U.S. PATENT DOCUMENTS

| | | | |
|---|---|---|---|
| 4,026,414 | 5/1977 | Ellinger | 250/223 B |
| 4,498,003 | 2/1985 | Cibis | 250/223 B |
| 4,606,635 | 12/1986 | Miyazawa et al. | 250/223 B |
| 4,697,076 | 9/1987 | Yoshida | 250/223 B |
| 4,731,649 | 5/1988 | Chang et al. | 250/223 B |
| 4,945,228 | 7/1990 | Juvinall et al. | 250/223 B |

Primary Examiner—David C. Nelms
Assistant Examiner—John R. Lee
Attorney, Agent, or Firm—McCormick, Paulding & Huber

[57] ABSTRACT

Photographs for detecting defects in the upper end face of the lip (43) of the mouth are taken by a camera (18) arranged on the axis of a bottle to be examined. An annular, coaxial light-conducting member (30), which is surrounded by a light source (28), is disposed between the lip (43) and the camera (18). It has a central viewing opening (40) with the shape of a double truncated cone (40a, 40b). The generated surface of the truncated cone (40a) adjacent to the lip forms a light exit surface (46a) to illuminate the lip (43). The angle of slope of the truncated cone (40a) is selected so that an annular truncated cone of light (52) falls on the upper face of the lip (43) and has an angle of incidence of about 45° in the middle thereof. This results in a dark-ground illumination of the lip (43). Should a defect be present in the region of the upper end face of the lip (43), this becomes visible as light on a dark background. Lateral defects of the lip (43) can also be detected by an additional light-conducting member (34).

15 Claims, 5 Drawing Sheets

APPARATUS FOR EXAMINING THE MOUTHS OF BOTTLES OR THE LIKE

BACKGROUND OF THE INVENTION

The invention relates to an apparatus for examining the mouths of bottles or the like of transparent material, in which a camera device is disposed on the axis of the bottle to be examined to take photographs of the mouth in order to detect defects, the apparatus also having a light source and at least a first light-conducting member which has a coaxial viewing opening and a first light exit surface to illuminate the mouth.

A known apparatus of this kind (U.S. Pat. No. 4,731,649) has a light-conducting member in the form of a translucent plate above which there are disposed a plurality of stroboscope lamps. Secured to the underside of the translucent plate are two prisms which direct light from the side inwards and obliquely upwards onto the rim of the mouth so that the camera device can take a video picture through the viewing opening in the translucent plate. The prisms are arranged at each side of a channel through which the mouth of the bottle to be examined is moved. In this case, the viewing opening is an oval opening and the translucent plate must supply additional light to illuminate the mouth from the front and rear because the prisms can only illuminate the mouth from the side. It is true that the viewing opening may also be circular but in either case it is impossible with the known apparatus to examine the upper end face of the mouth of the bottle, that is to say the lip in the case of a crown cork bottle. Since the mouth is only illuminated laterally in the known apparatus, the video camera can also only take a kind of collective picture which may contain numerous defects which are anywhere in the material of the bottle mouth or on the side thereof but not on the surface of the lip. The known apparatus is therefore more suitable for examining the mouths of bottles in a bottle manufacturing plant rather than in a bottling plant where work is carried on with considerably higher throughputs of bottles and defects which may impair the fluid-tightness of a bottle, particularly of a bottle to be refilled, are mainly of interest. In addition, the known apparatus works inaccurately because a uniform circular illumination is not possible with it. The illumination of the front and back of the mouth must necessarily be a compromise since the mouth is to be taken through between the prisms. In the known apparatus, this compromise can be accepted because the defects which are mainly of interest are those present in the screw thread on the bottle or in the mouth portion below the lip and are not easily visible looking in the direction along the axis of the bottle.

SUMMARY OF THE INVENTION

It is the object of the invention to develop an apparatus of the kind mentioned at the beginning so that it can supply, in a simple manner and in continuous operation, a reliable and uniformly illuminated picture of the upper end face of the lip of the mouth, particularly the lip of the mouth of a crown cork bottle or in general of containers of transparent material which have a mouth lip rounded at the top.

According to the invention, this problem is solved in that the first light-conducting member is made annular, that the viewing opening has the form of a first right truncated cone which widens out towards the face of the light-conducting member remote from the camera device and forms the light exit surface with its generated surface, and that the generating line of the first truncated cone forms an angle of slope with a value between 30° and 45°.

Since, in the apparatus according to the invention, the first light-conducting member is made circular and the viewing opening has the form of a first right truncated cone, the light-conducting member delivers the light radiated into it by the light source in the form of a truncated cone of light which becomes narrower towards the lip of the mouth of the bottle to be examined and which illuminates the lip of the mouth uniformly all over if this is arranged at a suitable height concentrically below the first light-conducting member. The precise value of the angle of slope which is selected depends on the height of the optical system above the mouth of the bottle and on its diameter.

Reflected rays of light leave the upper end face of the lip of the mouth at an angle which is the same as the angle of incidence. The camera device is arranged vertically above the bottle, in the axis of the bottle, and, since it photographs the mouth of the bottle at an angle of about 0°, it will receive reflected light only from the middle of the lip of the mouth and from the edges of the lip. Between the apex and the two edges of the lip of the mouth, the light is totally reflected so that these two regions appear to the camera in the form of dark rings which are enclosed by three light rings. Thus the apparatus according to the invention works with a dark-ground illumination. Only if a defect is present does this appear light on a dark background and can easily be perceived. Every defect actually produces scattered light which enters the camera. If defects occur not between but at the edges of the lip of the mouth, they appear to the camera as places with less illumination so that they are photographed as dark on a light background. Thus the apparatus according to the invention works with a combination of the said dark-ground illumination over the lip of the mouth and reflected illumination at its edges and in its middle.

In one development of the invention the total reflections taking place in the light-conducting member until the light finally reaches the light exit surface at the viewing opening can be better controlled, so that more light reaches the light exit surface and the illumination efficiency is improved as a result.

The angle of slope of 45° in a further development of the invention also corresponds to an angle of incidence of light of 45° in the middle of the upper end face of the lip of the mouth. This value of the angle is preferred because pictures can thus be taken of the mouth of the bottle which consist of symmetrical light and dark rings in which the maximum or minimum intensity lies in the middle of the ring in each case.

As a result of the selection of the length of the generating line of the first truncated cone in accordance with another development of the invention any loss of light during the illumination of the lip of the mouth is avoided.

In another development of the invention, all the external surfaces of the light-conducting member with the exception of the light entry surface and the light exit surface are covered by a black coating in order to avoid the incidence of stray light and light losses. The annular light source, which surrounds the light entry surface of the light-conducting member, serves simultaneously as a light source for a second circular light-conducting member for the lateral illumination of the lip when such second member is used. The second light-conducting member is preferably so arranged that its upper face is at the height of the upper edge of the sealing lip. It emits light at right-angles to the axis of the bottle. Thus the image of the top of the lip of the mouth produced by the first light-conducting member is completed by a lateral image of the mouth by the second light-conducting member. When two light-conducting members are used, defects are still made visible on the same principle as when only the first light-conducting member is used.

The third angle of slope of 45° in another development of the invention enables a maximum light yield to be achieved by means of the second light-conducting member.

The light-conducting member can be inexpensively produced from acrylic glass.

In order that the advantage of the uniform illumination of the mouth of the bottle to be examined and the possibility of continuous operation during the examination of bottles may also be retained when using a second light-conducting member, the second light-conducting member can be divided into a plurality of parts that can be moved apart and together in a plane at right angles to the axis of the bottle. Thus there is the possibility of opening the light-conducting member until the mouth has been moved under the first light-conducting member, and then closing the second light-conducting member for a short time. Another possibility would consist in moving the bottles to be examined under the light-conducting members, finally lifting them briefly up along their central axis to the optimum height for the examination process, and then lowering them again.

BRIEF DESCRIPTION OF THE DRAWINGS

Examples of embodiment of the invention are described in more detail below with reference to the drawings.

DESCRIPTION OF THE PREFERRED EMBODIMENTS

Figure 1:
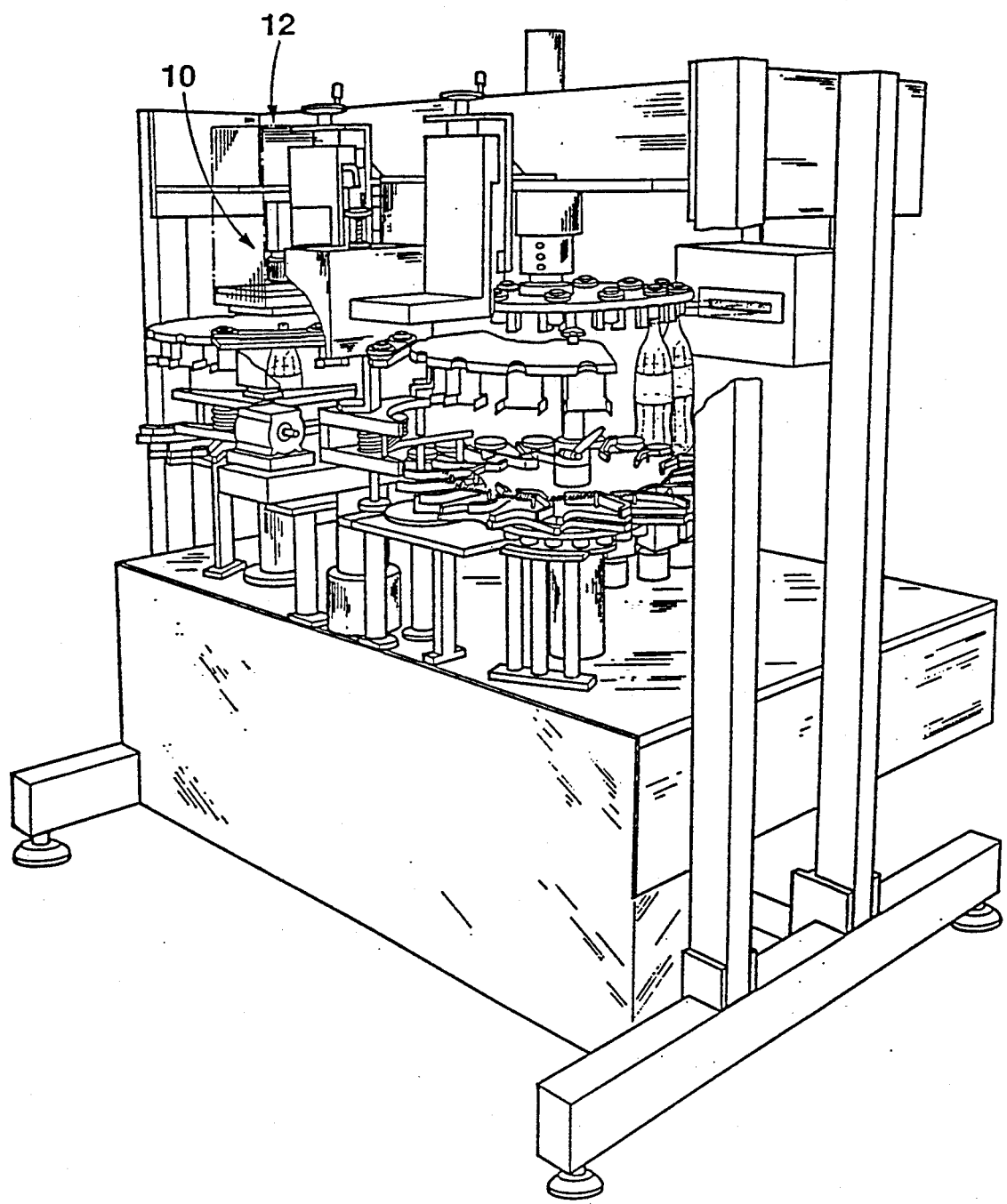
FIG. 1 shows a general view of a bottle examining machine which is provided with the examination apparatus according to the invention.

FIG. 1 shows a general view of a bottle examining machine which comprises an apparatus, designated as a whole by 10, for examining bottle mouths. The machine has two rotary tables which transfer the bottles from one to the other and move over two circular paths so that various examinations of the bottles can be carried out. The examination apparatus 10 is associated with the rotary table illustrated on the left in FIG. 1. In the station in which the mouth of a bottle is to be examined, a camera device designated as a whole by 12 is arranged on the axis of the bottle. According to the illustration in FIG. 2, this camera device comprises a housing 14 which is open at the bottom and which can be adjusted in height by means of a rotary spindle 16 and a handwheel 17. Disposed in the housing 14 is a 16-mm CCD video camera 18 which is adjustable in height jointly with the housing 14 or separately in a similar manner to the housing 14. At its lower end, the housing 14 carries an illumination system, designated as a whole by 20, for the lip of the bottle mouth, which system will now be described in more detail with additional reference to FIGS. 3 and 4.

Figure 2:
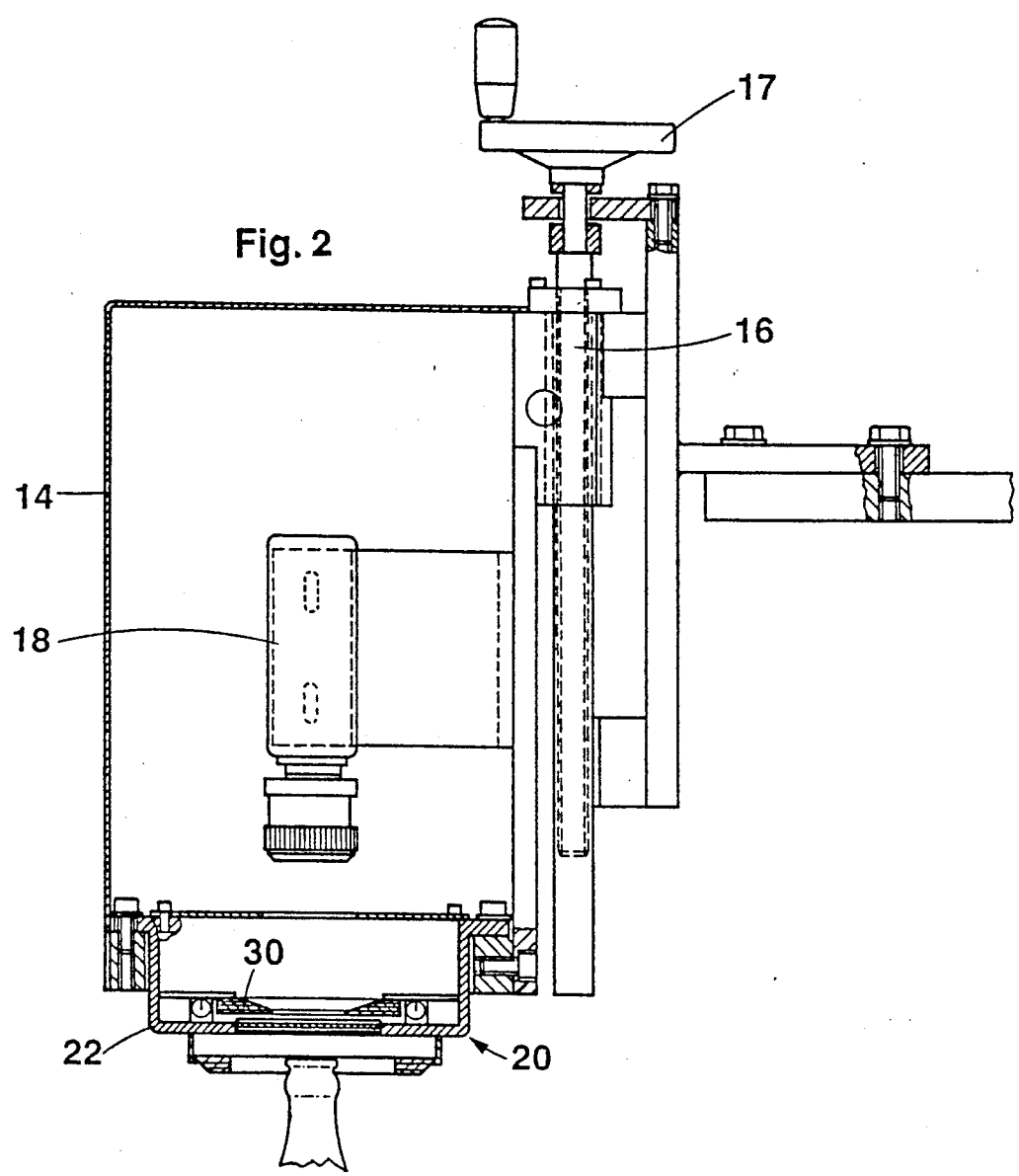
FIG. 2 shows, in a partial illustration, the mouth of a crown cork bottle to be examined, together with the illumination system and the camera device of the bottle examining machine.
Figure 3:
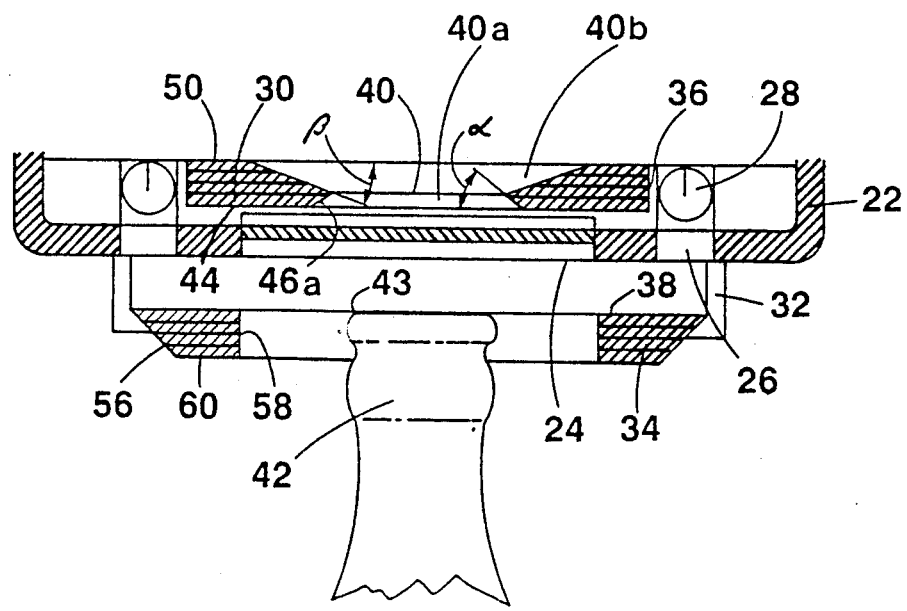
FIG. 3 shows, as an enlarged detail of FIG. 2, the mouth of the bottle with the illumination system arranged above it.

According to FIGS. 2 and 3, the illumination system consists of a cup-shaped holder 22 which is arranged with its centre axis in the axis of the bottle and has a sufficiently large central opening 24 at the bottom. The central opening is surrounded by an annular opening 26. A toroidal stroboscope lamp 28 is secured above the annular opening 26 as a light source. A first light-conducting member 30 is secured inwards of the stroboscope lamp 28, in the same plane as this. A second light-conducting member 34 is secured to a lower annular flange 32 of the cup-shaped holder 22. The light-conducting members 30, 34 are each annular in form and each is made of acrylic glass. The stroboscope lamp 28 is in line of sight communication with an outer circumferential surface 36 of the first light-conducting member 32, which surface forms its light entry surface. The stroboscope lamp 28 is likewise in line of sight communication with the upper face 38 of the second light-conducting member 34, which face forms its light entry surface. The first light-conducting member 30 has a coaxial viewing opening 40 through which the camera 18 can photograph the bottle mouth 42 and in particular its lip 43.

The viewing opening 40 has the shape of a double truncated cone consisting of a first truncated cone 40a and of a second truncated cone 40b. The truncated cone 40a widens out towards the face 44 of the first light-conducting member 30 remote from the camera device 12 and forms the light exit surface 46a of the light-conducting member 30 with its generated surface. The generating line of the first truncated cone 40a forms an angle of slope $\alpha$ with a value between 30° and 45° and in the example of embodiment illustrated has the preferred value of 45°.

The generating line of the second truncated cone 40b forms a second angle of slope $\beta$ which is a third to two thirds of the first angle of slope $\alpha$ and is preferably half the first angle of slope $\alpha$.

Figure 4:
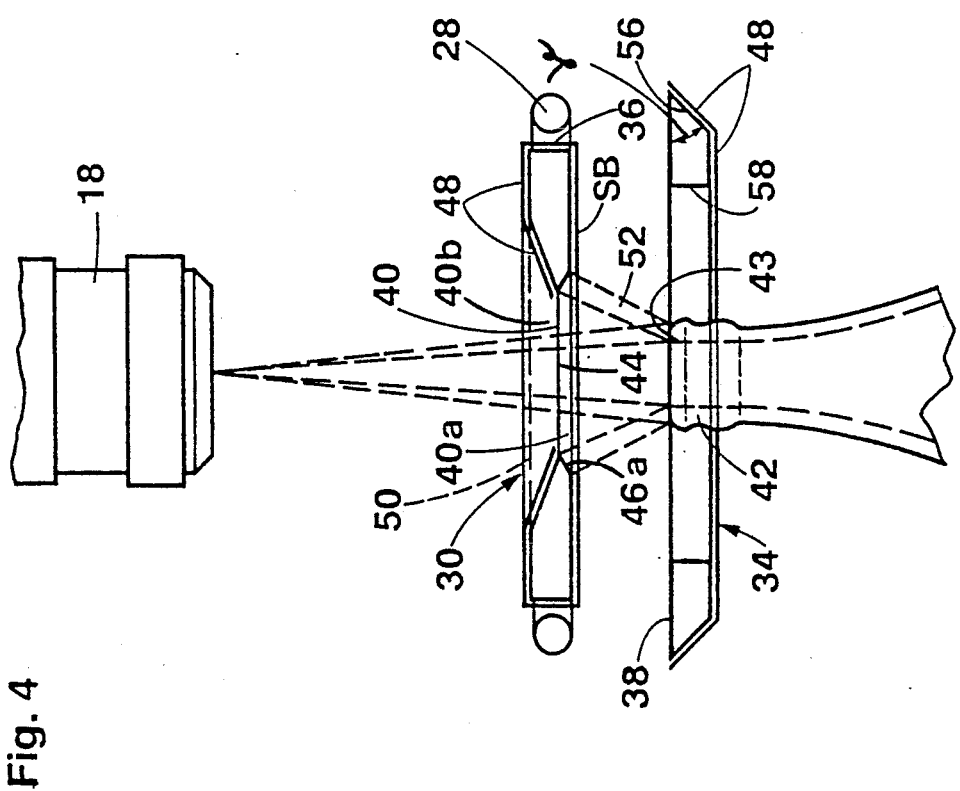
FIG. 4 shows the illumination system according to FIG. 3 and, in addition, the path of light rays during the illumination of the upper end face of the lip of the mouth.

In FIG. 4, the path of light rays between the first light-conducting member 30 and the camera 18 is drawn diagrammatically. It can be seen that the length of the generating line of the first truncated cone 40a is substantially equal to the width of the lip 43 of the mouth 42 of the crown cork bottle illustrated. The lower face 44, the upper face 50 and the peripheral face of the second truncated cone 40b are covered by black coatings which are indicated in FIG. 4 by the reference 48. The light entering the first light-conducting member 30 through the light entry surface 36 therefore reaches its light exit surface 46a practically completely without stray light being added or being scattered to the outside. The light emerging at the exit surface 46a forms an annular truncated cone of light 52 which falls on the lip 43. In the middle of the lip 43, the angle of incidence of the light is about 45° so that no light is reflected from the middle of the lip 43 to the camera 18, but only from the edges of the lip 43 as was explained at the beginning. Only if a defect is present will light also be reflected from the middle region of the upper face of the lip 43 to the camera 18.

Figure 5:
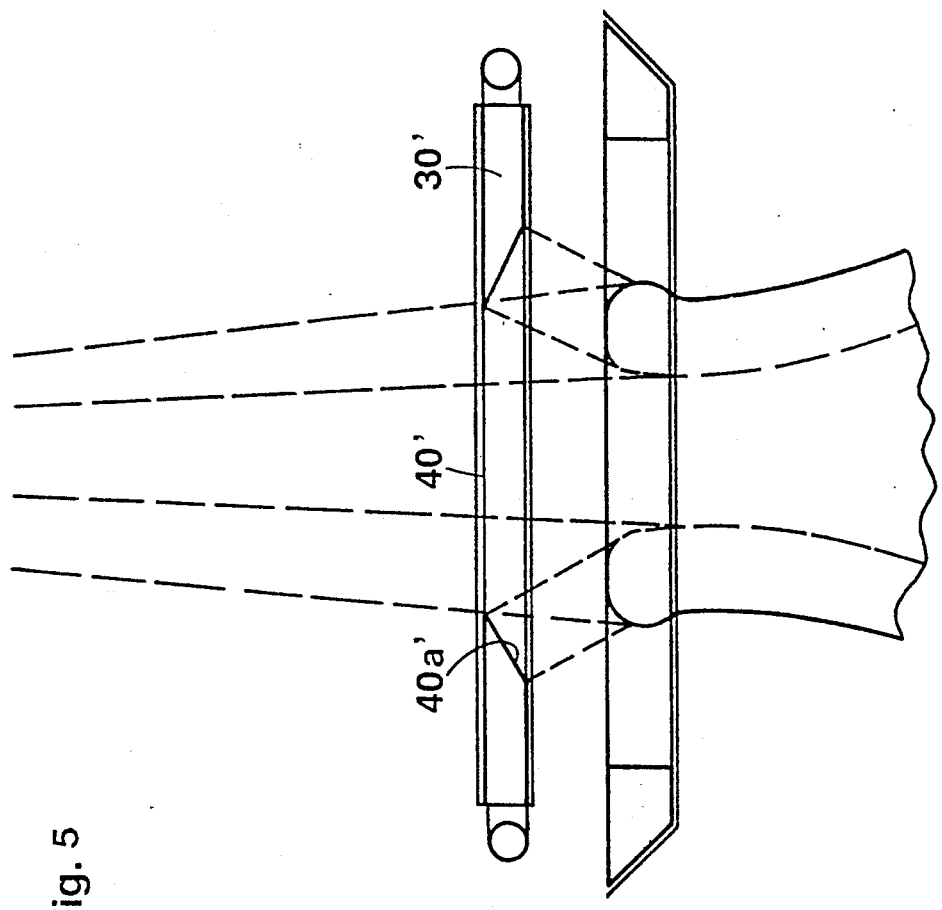
FIG. 5 shows an arrangement as in FIG. 4 but with a first light-conducting member wherein the viewing opening has the shape of a simple right truncated cone.

For the operation of the examining apparatus 10 described here, the first light-conducting member would only need a viewing opening with the shape of the first right truncated cone 40a. In FIG. 5, such a light-conducting member 30' with such a viewing opening 40' in the form of a right truncated cone 40a' is illustrated. The form of embodiment illustrated in FIG. 4, wherein the viewing opening 40 has the form of a double truncated cone 40a, 40b is, however, preferred.

The first light-conducting member 30 or 30' is sufficient for detecting defects on the upper face of the bottle mouth 42. If, however, defects on the lateral faces of the lip also have to be additionally detected, the second light-conducting member 34, which will now be described in more detail, may appropriately be used in addition.

The second light-conducting member 34, coaxial with the first light-conducting member 30, has a larger external diameter than the first light-conducting member, as is illustrated in the drawings. As a result, there is the possibility of using one and the same stroboscope lamp 28 as a light source for both light-conducting members. Instead of this, however, a separate light source (not illustrated) may also be used for the second light-conducting member 34. Photographs of the upper face and of the lateral face of the lip 43 could therefore be taken alternately by switching on the light sources of the first and second light-conducting members alternately.

The second light-conducting member 34 has a frusto-conical outer peripheral surface 56 widening out towards the first light-conducting member 30, and a cylindrical inner surface 58 which forms a second light exit surface for the lateral illumination of the lip 43. The thickness of the second light-conducting member 34 is at least as great as the depth of the lip 43 of the mouth 42 of a crown cork bottle to be examined (see FIG. 5) or about twice as great as the depth of this lip (see FIGS. 3 and 4). The upper face 38 of the second light-conducting member 34 is arranged at the height of the upper edge of the lip 43 as mentioned above. The peripheral surface 56 and the lower face 60 are again covered by a black coating 48 which is indicated in FIG. 4.

The generating line of the generated surface 56 forms an angle of slope ($\gamma$) of 45° (see FIG. 4). The light from the stroboscope lamp 28, which enters the second light-conducting member 34 parallel to the axis of the bottle, through the upper face 38, is therefore reflected on the generated surface 56 and reaches the outer side of the lip 43 at right-angles to the axis of the bottle. So long as the outer wall of the lip 43 has no defects, the light ring produced by means of the second light-conducting member 34 and photographed by the camera 18 remains uniformly bright. Should a defect be present, this light ring contains dark places making the defect visible.

During the examination for defects, either the bottle is raised until it reaches the position illustrated in the drawings or the second light-conducting member 34 is made in a divided form (not illustrated). In this case, the parts of the second light-conducting member 34 can be moved apart and together in a plane at right-angles to the axis of the bottle. With the parts of the second light-conducting member 34 moved apart, the bottle is moved into the position illustrated in the drawings and in which the examination is effected, whereupon the parts are moved together so that the second light-conducting member 34 assumes the position shown in FIGS. 4 or 5. Furthermore, it would be possible to convey the bottle horizontally and to move the examination apparatus 10 vertically to the appropriate height relative to the mouth 42 of the bottle for carrying out the examination process.

Figure 6:
FIG. 6 shows a photograph of a mouth lip free from defects taken with the camera device.
Figure 7:
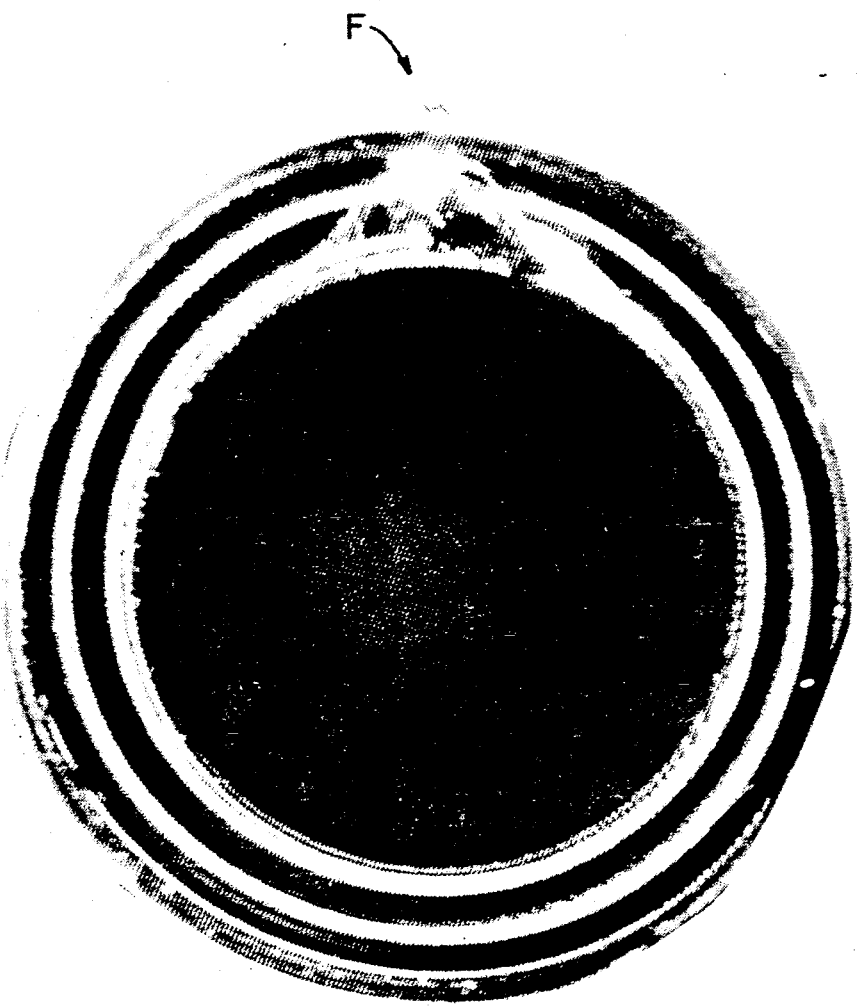
FIG. 7 shows a photograph of a mouth lip with a defect taken by the camera device.

FIG. 6 shows a photograph of a bottle mouth without a defect taken by the camera 18 whereas FIG. 7 shows the photograph of a bottle mouth with a defect F. The photograph taken by the camera 18 is evaluated according to gray scale values. For this purpose, specific regions in the form of annuli are defined which contain a certain number of picture elements (pixels), for example 40 picture elements from which the average gray scale value is determined in comparison with the neighbouring region. In addition, a maximum threshold value is fixed for the difference in gray scale values between two adjacent regions. If, during the examination of a bottle, a difference in gray scale values is found which is greater than this threshold value, the bottle is rejected as faulty.

I claim:

1. An apparatus for examining the mouths of bottles or the like of transparent material, in which a camera device is disposed on the axis of a bottle to be examined to take photographs of the mouth in order to detect defects, the apparatus also having a light source and at least a first light-conducting member which has a coaxial viewing opening and a first light exit surface to illuminate the mouth, characterized in that said light-conducting member is made annular, that the viewing opening has the shape of a first right truncated cone which widens out towards the face of said light-conducting member remote from the camera device and forms the light exit surface with its generated surface, and that a generating line of said truncated cone forms a first angle of slope ($\alpha$) with a value between 30° and 45°.

2. An apparatus according to claim 1, characterized in that the viewing opening has the shape of a double truncated cone which is formed from the first truncated cone and from a second truncated cone which widens out towards the face of the first light-conducting member facing the camera device.

3. An apparatus according to claim 1, characterized in that the first angle of slope ($\alpha$) is 45°.

4. An apparatus according to claim 2, characterized in that a generating line of the second truncated cone forms a second angle of slope ($\beta$) which is one a third to two thirds of the first angle of slope ($\alpha$).

5. An apparatus according to claim 4, characterized in that the second angle of slope ($\beta$) is one-half the first angle of slope ($\alpha$).

6. An apparatus according to claim 1, characterized in that the length of the generating line of the first truncated cone is substantially equal to the width of a lip of the mouth of a bottle.

7. An apparatus according to claim 1, characterized in that the light source is arranged in the form of a ring around the outer circumferential surface of the light-conducting member, and that the two axial end faces of the light-conducting member are covered by a black coating.

8. An apparatus according to claim 7, characterized in that the ring consists of a plurality of individual stroboscope lamps.

9. An apparatus according to claim 7, characterized in that the ring consists of a single torodial stroboscope lamp.

10. An apparatus according to claim 1, characterized by a coaxial second annular light-conducting member which is arranged adjacent to the first light-conducting member at the side thereof remote from the camera device, has a larger external diameter than the first light-conducting member, and has a first generated surface widening out towards the first light-conducting member and a cylindrical second surface which forms a second light exit surface for the lateral illumination of a lip of the mouth of a bottle to be examined.

11. An apparatus according to claim 10, characterized in that the thickness of the second light-conducting member is about twice as great as the depth of the lip of the mouth of the bottle to be examined.

12. An apparatus according to claim 10, characterized in that the first generated surface and the face of the second light-conducting member remote from the first light-conducting member are covered by a black coating.

13. An apparatus according to claim 10, characterized in that a generating line of the said first generated surface of said second annular light-conducting member forms an angle of slope ($\gamma$) of 45°.

14. An apparatus according to claim 1, characterized in that the material of the at least first light-conducting member is acrylic glass.

15. An apparatus according to claim 10, characterized in that the second light-conducting member is divided into a plurality of parts that can be moved apart and together in a plane at right-angles to the axis of a bottle to be examined.

* * * * *